(12) United States Patent
Powers et al.

(10) Patent No.: US 10,960,194 B2
(45) Date of Patent: Mar. 30, 2021

(54) TRANSDUCER PLACEMENT AND REGISTRATION FOR IMAGE-GUIDED SONOTHROMBOLYSIS

(71) Applicant: KONINKLIJKE PHILIPS N.V., Eindhoven (NL)

(72) Inventors: Jeffry Earl Powers, Bothell, WA (US); William Tao Shi, Cambridge, MA (US); John Douglas Fraser, Bothell, WA (US); Ralf Seip, Cambridge, MA (US); Francois Guy Gerard Marie Vignon, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1227 days.

(21) Appl. No.: 14/901,293

(22) PCT Filed: Jun. 25, 2014

(86) PCT No.: PCT/IB2014/062578
§ 371 (c)(1),
(2) Date: Dec. 28, 2015

(87) PCT Pub. No.: WO2014/207665
PCT Pub. Date: Dec. 31, 2014

(65) Prior Publication Data
US 2016/0151618 A1 Jun. 2, 2016

Related U.S. Application Data

(60) Provisional application No. 61/840,752, filed on Jun. 28, 2013.

(51) Int. Cl.
*A61M 37/00* (2006.01)
*A61B 8/06* (2006.01)
(Continued)

(52) U.S. Cl.
CPC .......... *A61M 37/0092* (2013.01); *A61B 8/06* (2013.01); *A61B 8/085* (2013.01); *A61B 8/0816* (2013.01);
(Continued)

(58) Field of Classification Search
CPC .... A61M 37/0092; A61B 8/06; A61B 8/0816; A61B 8/085; A61B 8/4209;
(Continued)

(56) References Cited

U.S. PATENT DOCUMENTS 5,497,540 A * 3/1996 Venkataramani ..... B06B 1/0622
29/25.35
5,520,188 A * 5/1996 Hennige ............... A61B 8/0833
310/367
(Continued)

FOREIGN PATENT DOCUMENTS

EP 1449563 A1 8/2004
JP 05221052 A 8/1993
(Continued)

*Primary Examiner* — Amelie R Davis
*Assistant Examiner* — John Denny Li (57) ABSTRACT

An apparatus for ultrasound irradiation of a body part (208) includes a first ultrasound transducer (216), and a second ultrasound transducer (212) mounted oppositely, and is configured: a) such that at least two ultrasound receiving elements, for determining a relative orientation of the first to the second transducer, are attached to the first transducer; b) for a beam, from the first transducer, causing cavitation, and/or bubble destruction of systemically circulating microbubbles, within the body part; or c) both with the attached elements and for the causing. The apparatus registers, with said first transducer, the second transducer, by using as a reference respectively the features a) and/or b). A detachable subsystem includes either a therapy or imaging transducer, to form a combination imaging and therapy system, the subsystem being configured for removable cou- (Continued)

pling to correspondingly an imaging or therapy subsystem comprising a head frame (204) to which is mounted an imaging or therapy transducer, the imaging or therapy subsystem for registering the imaging or therapy transducer, one to the other, by the above method.

15 Claims, 5 Drawing Sheets

(51) Int. Cl.
*A61B 8/08* (2006.01)
*A61N 7/00* (2006.01)
*A61B 8/00* (2006.01)
*A61B 34/20* (2016.01)
*A61B 90/00* (2016.01)

(52) U.S. Cl.
CPC .......... *A61B 8/4209* (2013.01); *A61B 8/4254* (2013.01); *A61B 8/4483* (2013.01); *A61B 8/481* (2013.01); *A61N 7/00* (2013.01); *A61B 8/461* (2013.01); *A61B 8/5238* (2013.01); *A61B 2034/2063* (2016.02); *A61B 2090/378* (2016.02); *A61N 2007/0039* (2013.01); *A61N 2007/0052* (2013.01)

(58) Field of Classification Search
CPC ..... A61B 8/4254; A61B 8/4483; A61B 8/481; A61B 8/461; A61B 8/5238; A61B 2034/2063; A61B 2090/378; A61N 7/00; A61N 7/02; A61N 2007/0039; A61N 2007/0052
See application file for complete search history.

(56) References Cited

U.S. PATENT DOCUMENTS

| | | | |
|---|---|---|---|
| 6,511,428 B1 | 1/2003 | Azuma et al. | |
| 2004/0220476 A1* | 11/2004 | Fehre | A61B 8/08 600/459 |
| 2004/0267127 A1* | 12/2004 | Abend | G01S 7/52061 600/450 |
| 2005/0154309 A1 | 7/2005 | Etchells | |
| 2007/0083120 A1* | 4/2007 | Cain | A61B 17/22004 600/439 |
| 2007/0156050 A1* | 7/2007 | Barnes | G01S 15/8925 600/447 |
| 2007/0239000 A1 | 10/2007 | Emery | |
| 2008/0119727 A1* | 5/2008 | Barbagli | A61B 8/0833 600/424 |
| 2008/0312561 A1* | 12/2008 | Chauhan | A61B 8/4209 601/2 |
| 2010/0010393 A1 | 1/2010 | Duffy | |
| 2010/0160779 A1* | 6/2010 | Browning | A61B 5/02007 600/439 |
| 2012/0035476 A1* | 2/2012 | Barthe | A61B 8/0858 600/439 |
| 2012/0123243 A1* | 5/2012 | Hastings | A61B 8/0841 600/411 |
| 2012/0165670 A1 | 6/2012 | Shi | |
| 2015/0141734 A1* | 5/2015 | Chapelon | A61N 7/02 600/2 |
| 2015/0233811 A1* | 8/2015 | Strohm | G01N 15/14 73/601 |

FOREIGN PATENT DOCUMENTS

| | | |
|---|---|---|
| WO | 2012042494 A1 | 4/2012 |
| WO | 2015092604 A1 | 6/2015 |

* cited by examiner

TRANSDUCER PLACEMENT AND REGISTRATION FOR IMAGE-GUIDED SONOTHROMBOLYSIS

CROSS-REFERENCE TO PRIOR APPLICATIONS

This application is the U.S. National Phase application under 35 U.S.C. § 371 of International Application No. PCT/IB/2014/062578, filed on Jun. 25, 2014, which claims the benefit of U.S. Provisional Patent Application No. 61/840,752, filed on Jun. 28, 2013. These applications are hereby incorporated by reference herein.

FIELD OF THE INVENTION

The present invention relates to registering one ultrasound transducer to another and, more particularly, to registering transducers mounted on opposite sides of a body part.

BACKGROUND OF THE INVENTION

It has been known for many years that ultrasound in combination with thrombolytic drugs, in particular tissue plasminogen activator (tPA) can aid in the dissolution of blood clots that cause ischemic stroke. However, tPA has many side effects and can be deadly when used in a hemorrhagic (bleeding) stroke patient and so requires a CT to rule out hemorrhage before its use. Ultrasound in combination with microbubble contrast agents has also been shown to lyse blood clots with potentially fewer adverse effects. This effect is commonly referred to as sonothrombolysis (STL).

Transcranial imaging has long been used to diagnose cerebrovascular diseases such as stroke with diagnostic ultrasound systems. Strokes nearly always occur on one side of the brain or the other. The most common clinical diagnosis of stroke is weakness on one side, implying a stroke on the opposite side since the right side of the brain controls motor function on the left side of the body and vice versa. Approximately 70% of all ischemic strokes occur in the middle cerebral artery (MCA), a major vessel, and strokes here are especially devastating. The MCA is located behind the temporal bone (at a depth of approximately 3-5 cm), the thinnest part of the skull and hence the least attenuating for ultrasound.

Commonly-assigned U.S. Patent Publication No. 2010/0160779 to Browning et al. (hereinafter "the Browning application"), the entire disclosure of which is incorporated herein by reference, discloses a headset into which are mounted transducers for STL.

SUMMARY OF THE INVENTION

It is well known that the skull is highly attenuative, especially at frequencies above about 1 MHz. Most studies of STL without tPA require significantly more power than is typically used during imaging. Since the size and exact position of the blood clot may not be known exactly, a broad coverage would optimally be used to insonify a large area in the presumed location of the clot. Microbubbles are destroyed during the process, so the ideal acoustic field would be a broad beam at relatively high intensity for a short duration (0.1-1000 milliseconds), followed by a pause of up to 30 sec to allow bubbles to return to/replenish the region of interest (ROI). A broad therapeutic coverage also increases the overall positioning robustness of the system, as small displacements or misalignment of the therapeutic beam with the clot target region would not negatively affect the delivery of the treatment, as the clot would continue to be located within the coverage of the therapy beam.

Transcranial ultrasound imaging is commonly done at about 1.5-2.0 MHz as the best trade-off of between skull penetration and resolution. For axial resolution, broadband transducers are usually used, which may be less efficient at overall power transmission. Even the lens on the front of the transducer which provides focusing in elevation is absorptive. Imaging transducers are not designed to be particularly efficient, as image quality is the driving concern and input power rarely considered.

In order to cover a large area for stroke therapy with an ultrasound transducer two methods can be used:
1. The beam can be specially designed with a broad coverage. For instance, the beam can be defocused, but this significantly reduces the local instantaneous power in the ROI.
2. The beam (with relatively narrow coverage) can be step-scanned around the region of interest, but a beam in one location is likely to destroy bubbles in adjacent locations, which may require much longer therapy times while the bubbles replenish the ROI.

To minimize attenuation due to the brain tissue of the imaging beam, and to maintain good image quality, it is advantageous to place the imaging transducer on the ipsilateral temporal window (resulting in a shorter distance between the imaging transducer and the clot in the ROI), and to place the therapy transducer on the contralateral temporal window. The imaging transducer is employed for locating the occlusion region (ROI) and guiding the therapeutic beam toward the ROI. While arrangements where both imaging- and therapeutic transducers on the same temporal window are possible (arranged concentrically, or side-by-side, for example), the relatively small size of the temporal window typically prevents this. Employing separate transducers for imaging and therapy delivery is thus desired, as this further allows for tailoring their acoustic characteristics separately (and optimally) for their different intended purposes. A discussion about attaining the optimal acoustic window in cranial imaging is found in commonly-assigned U.S. Patent Publication No. 2012/0165670 to Shi et al. (hereinafter "the Shi application"), the entire disclosure of which is incorporated herein by reference.

In Browning, both transducers are capable of both imaging and therapy; whereas, it is proposed herein to specialize one for imaging and the other for therapy, with the imaging transducer being placed on the same side of the cranium as the probable stroke. Accordingly, the Browning therapeutic beam within the imaging field from the same transducer, as seen in Browning FIG. 4, would not apply herein.

Also, the Browning therapeutic beam vector graphic 142 within the imaging plane 140 as shown in Browning FIG. 5 is not used in the proposal herein; instead, an overlay of the contour of the contralateral therapy beam is displayed, as in commonly-assigned International Publication Number WO 2012/042494 to Vignon et al. (hereinafter "the Vignon application"), the entire disclosure of which is incorporated herein by reference. Here, the Browning Doppler processor 28 is supplemented with the function of processing cavitation data, like the cavitation processor 28 of the Vignon application. Here, however, some of the processing features of the cavitation processor 28 are optional. In particular, in Vignon, the focus is on spatially detecting beneficial, and less than beneficial, areas of cavitation and microbubble destruction; here, optionally a simpler signal analysis is needed just for the therapy beam contour detection, in order to spatially register both imaging and therapy transducers. In some embodiments herein, the detection is for inter-transducer registration purposes. As in Vignon, the overlay function of the cavitation processor 28 draws input from the B-mode processor 26.

In Browning, additionally, one of the focuses is on patient monitoring for intra-cranial blood flow changes. The speaker 42, flow change detector 50, and image store 52 are optional for what is proposed herein; although, as in Vignon, an inertial cavitation detector 50 can substitute for the flow change detector, for monitoring of safe and effective levels of cavitation.

Herein, the focus is on inter-transducer registration, as discussed in more detail below. The mechanical index (MI) and beam steering (BEAM STEER) functions in Browning FIG. 1 are controlled by one or more registration modules of respective alternative embodiments, as well as by a user interface such as the user interface 38 of Browning. A controller of the modules also controls optional motorized assemblies for each transducer or both.

The focus on inter-transducer registration in the current proposal is as a result of separating functions into respectively specializing transducers.

With the separation of transducer function, and given the adjustability of the transducers mounted in the head frame to, for example, pivot in a desired direction in some embodiments of what is proposed herein, registration of one transducer to the other allows for accurate targeting of the clot in the ROI. Even in the case of electronic steering for both transducers, the feature of the headset being adjusted to each individual patient is compensatingly corrected by the co-registration of the transducers during initialization. In one embodiment, registration relies on cavitation, and/or microbubble destruction, caused via the therapy transducer and detection of these effects by the imaging transducer. In another embodiment, ultrasound receiving elements on the periphery of the face of the therapy transducer allow for registration without the use of microbubbles.

The head frame, in some embodiments, differs from that shown in Browning FIGS. 2A, 2B in that it may be reversible such as the head frame 128 shown in FIG. 1 of the Shi application.

The head frame can also be configured for modularity in that imaging or therapy subassemblies or subsystems may be removed for deployment elsewhere. For example, once imaging has been used to direct the therapy beam to the clot or other treatment location, the imaging transducer may be disengaged. The detachable subsystem having the imaging transducer may, for example, after some time period, be re-attached to the patient, to determine treatment progress at a later point in time. This is one of the benefits of the separation of function. Thus, for example, each Browning array 10a, 10b is housed within its own fluid-filled enclosure and is configured for motor-driven pivotable motion. The enclosure is, where it is to contact the temporal bone area of the patient's skull, flexible and acoustically transparent. Motor and transducer control cabling to the enclosure, the enclosure, and its contents form a unit, i.e., respectively an imaging or therapy detachable subsystem. At the other end, the cabling attaches to and detaches from a connection to the above-mentioned controller. Coupling fluid inlet-and-outlet tubing to the enclosure, for varying the fluid volume in, for example making the acoustic connection conformal, is connectable at the other end to a water degassing device if the fluid is water. An example of such a degassing device that cools the coupling fluid, a feature that is especially useful for the therapy subassembly, is found in U.S. Patent Publication No. 2005/0154309 to Etchells et al., the entire disclosure of which is incorporated herein by reference. When the detachable subsystem is to be attached or detached, the controller and the degassing device are notified responsive to an indication by the clinician via the Browning user control 38.

The microbeamformers 12a, 12b in Browning are not needed here. For wide angle steering, high frequency, and good resolution, an imaging matrix transducer needs over 1,000 elements. This requires integrating electronics within the transducer itself to avoid having so many wires in the cable, which are usually limited to 128. To reduce heat dissipation, the transmitting electronics in matrix transducers have limited power output capabilities. Since only limited steering and focusing are required, the matrix transducer herein meets the requirements with no more than 128 elements, making it less expensive and able to handle much higher power levels as it can be driven directly from the system transmitting electronics, requiring none in the housing.

In accordance with an aspect of what is proposed herein, an apparatus for ultrasound irradiation of a body part includes a first ultrasound transducer, and a second ultrasound transducer that, with respect to said body part, is mounted oppositely to said first transducer. The apparatus is configured with at least one of two features. The first feature is that at least two ultrasound receiving elements, for determining a relative orientation of the first to the second transducer, are attached to the first transducer. The second feature is for a beam, from the first transducer, causing cavitation, and/or bubble destruction, within the body part. The apparatus is further configured for registering, with the first transducer, the second transducer, by using as a reference respectively: i) two or more of the elements; and/or ii) correspondingly the cavitation and/or the destruction, i.e., an acoustic signal from the systemically circulating microbubbles, that signal being dynamically representative of the cavitation and/or the destruction.

In a sub-aspect, the irradiation entails medical ultrasound treatment, and the first transducer includes a therapy transducer.

In a further sub-aspect, the first transducer is specialized for therapy, and the second transducer is specialized for imaging.

In one sub-aspect, the first transducer is a therapy transducer to which the at least two elements are attached.

In a further sub-aspect, the first transducer has a face for acoustically interfacing with the body part, the face has a periphery, and the at least two receiving elements are disposed at the periphery.

As a yet further sub-aspect, the apparatus is further configured for forming, via the second transducer, an elevational plane of an ultrasound image. From among the at least two elements there is a series of receiving elements at the periphery spaced apart from each other by respective gaps small enough such that two or more of the at least two elements are within the plane irrespective of a rotational orientation of the plane.

In another sub-aspect, the registering involves, automatically and without need for user intervention, a) electronically rotating an elevational plane of an ultrasound image; and b) receiving, via the elements during the rotating, a radiofrequency signal for detection of when, during the rotating, the signal received by the elements is maximal.

In a related sub-aspect, the registering includes estimating, based on output of the elements, an orientation, and distance, of the first transducer with respect to the second transducer.

In still another sub-aspect, the apparatus further includes a motorized assembly and is configured for moving, via the assembly, the first transducer, automatically and without need for user intervention, to point in a different direction until an alignment criterion is met, based on output of the elements.

As yet another sub-aspect, the apparatus is further configured for three-dimensional (3D) imaging via the second transducer. The registering includes scanning ultrasound pulses, via the second transducer, with the second transducer being held fixed in place.

As a sub-aspect of this, the apparatus is further configured for, concurrently with the scanning, operating two or more of the at least two receiving elements to receive ultrasound. The registering is based on content of the received ultrasound signal.

In an alternative or complementary sub-aspect, the registering entails focusing, via the second transducer, on a specific target within the body part and using two or more of the at least two receiving elements for detecting side scattering from the target.

In another, particular sub-aspect, the apparatus is further configured for the beam causing the cavitation and/or bubble destruction, and for the registering using correspondingly the cavitation and/or bubble destruction.

In a further sub-aspect, the registering includes scanning via the first transducer, with the second transducer being held fixed in place.

In a related sub-aspect, said registering entails scanning, via the first transducer, for the above-mentioned causing. It further entails using, in conjunction with the scanning, the second transducer to monitor an outcome of the causing.

The apparatus being configured, in a further sub-aspect, for, automatically and without need for user intervention, scanning, via the first transducer, until, based on imaging via the second transducer, it is determined that a current direction of the scanning brings the transducers into registration.

With the body part being a head of a human or of an animal, the apparatus further includes, in a sub-aspect, a wearable head frame configured for the mounting of both transducers. The apparatus is configured for the registering while the head frame is worn on the head.

In a further sub-aspect, the second transducer is movably mounted to the head frame, and the registering includes fixing the second transducer in place in the head frame.

In another particular sub-aspect, the first transducer is movably mounted to a head frame. The apparatus is configured for mechanical movement of said first transducer to, in performance of said registering, scan a volume within said body part.

In one other sub-aspect, the apparatus further includes a display. The apparatus is further configured for imaging the body part via the second transducer and for displaying, via the display, an image of the body part.

In another aspect, a detachable ultrasound subsystem includes either an ultrasound therapy transducer or an ultrasound imaging transducer. To form a combination imaging and therapy system, the subsystem is configured for removable coupling to correspondingly an imaging or a therapy subsystem. The imaging or therapy subsystem includes a head frame to which is mounted an imaging or therapy transducer. The imaging or therapy subsystem is configured for registering the imaging or therapy transducer, one to the other, by at least one of: a) detecting cavitation, and/or bubble destruction; and b) output of at least two ultrasound transducer elements attached to the therapy transducer and configured so as to be devoted to receiving ultrasound.

In one other, complementary aspect, an imaging or therapy subsystem includes a head frame and correspondingly, an imaging or therapy transducer mounted to the head frame. The imaging or therapy subsystem is configured for forming a combination imaging and therapy system by registering the imaging or therapy transducer to the other of the imaging or therapy transducer of a detachable subsystem. The registering is by at least one of: a) detecting cavitation, and/or bubble destruction; and b) output of at least two ultrasound transducer elements attached to the therapy transducer and configured so as to be devoted to receiving ultrasound.

In complementary, related versions, for an apparatus for ultrasound irradiation of a body part a computer readable medium or alternatively a transitory, propagating signal is part of what is proposed herein. These are in the context of an apparatus that includes a first ultrasound transducer, and a second ultrasound transducer that, with respect to the body part, is mounted oppositely to the first transducer. The apparatus is configured with at least one of two features. The first feature is that at least two ultrasound receiving elements, for determining a relative orientation of the first to the second transducer, are attached to the first transducer. The second feature is for a beam, from the first transducer, causing cavitation, and/or bubble destruction, within the body part. A computer program embodied within a computer readable medium as described below, or, alternatively, embodied within a transitory, propagating signal, has instructions executable by a processor for performing the act of: registering, with the first transducer, the second transducer, by using as a reference respectively: i) two or more of the elements of the first feature; and/or ii) the cavitation and/or the destruction of the second feature.

Details of the registration technology for contralaterally mounted transducers are set forth further below, with the aid of the following drawings, which are not drawn to scale.

DETAILED DESCRIPTION OF EMBODIMENTS

Figure 1:
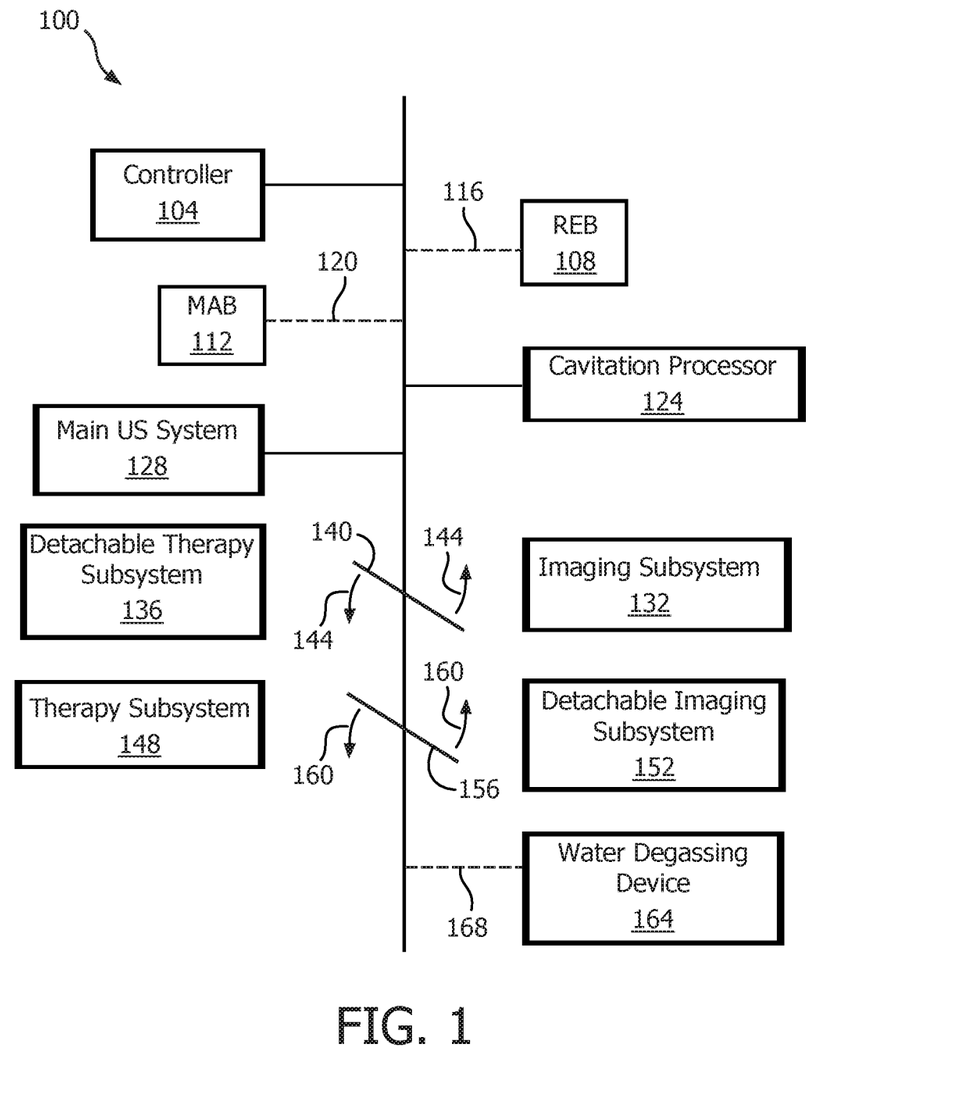
FIG. 1 is a schematic diagram of an exemplary apparatus serving as a combination imaging and therapy system in accordance with the present invention.

FIG. 1 depicts, in illustrative and non-limitative example, an apparatus 100 serving as a combination imaging and therapy system. It includes a controller 104, a receiving-element-based (REB) registration module 108, and/or a microbubble-activity-based (MAB) registration module 112. The broken lines 116, 120 to the REB and MAB registration modules are to imply that the two modules 104, 108 are alternatives or can be operational within the same device. Also part of the apparatus 100 are a cavitation processor 124 which is mentioned herein above, and a main ultrasound system 128 that corresponds to FIG. 1 of the Browning application with the changes discussed herein above. The main ultrasound system 128 therefore contains the user interface 38, the display 40, etc. in FIG. 1 of the Browning application. An additional part of the apparatus 100 is an imaging subsystem 132 and its complementary detachable therapy subsystem 136. A first illustrative line segment 140 is rotatable, according to first arrows 144, into and out of engagement with the two subsystems 132, 136, to signify that the two subsystems are optional. An alternative, or supplemental, option is a therapy subsystem 148 and its counterpart detachable imaging subsystem 152. They are correspondingly represented by a second illustrative line segment 156 rotatable as shown by second arrows 160. The apparatus 100 can further include a water degassing device 164, if water is the acoustic coupling medium utilized. The conditionality is represented by the broken line 168.

Figure 2:
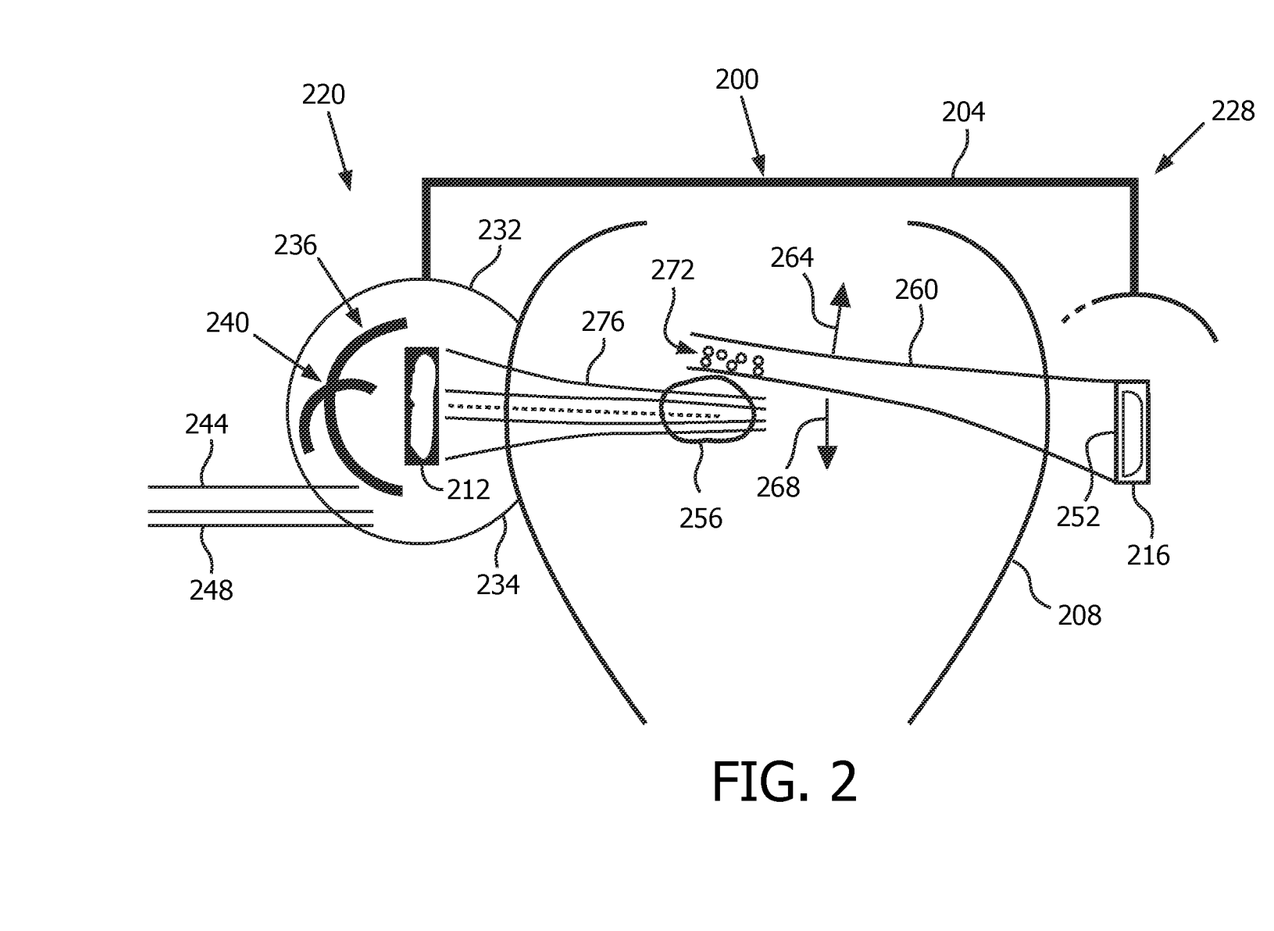
FIG. 2 is a schematic and conceptual diagram exemplary of a headset with ultrasound therapy and imaging transducers mounted on opposite sides of the skull, and microbubble-activity-based inter-transducer registration, in accordance with the present invention.

FIG. 2 shows a transducer mounting arrangement 200 that includes a head frame or headset 204, in which the two transducers are mounted on opposite sides of the skull. It is wearable on a head 208 of a human patient or animal. Mounted to the ipsilateral side is an imaging transducer 212. Mounted to the contralateral side is a therapy, or "therapeutic", transducer 216. The imaging transducer 212 may be applied to the side of the head 208 closest to the probable lesion (ipsilateral side), to enhance visual resolution. Therapy beams applied from the other side (contralateral side) of the head 208 can be made relatively broad, and therefore robust against misalignment. The therapy transducer 216 could be as simple as an unfocused piston transducer which would flood the area on the opposite side with the clot-lysing therapy beams. This would primarily be applicable to MCA strokes, as the MCA is typically located 3-5 cm behind the temporal window. For more flexibility (to accommodate patient-to-patient vasculature variability) and to accommodate strokes occurring in other vessels, the therapy transducer 216 would, like the imaging transducer 212, be a matrix transducer to allow limited steering and focusing and would operate at a lower frequency than the imaging transducer, say 1 MHz.

Alternatively, it is also possible to completely switch the position of both transducers: in this scenario, the imaging transducer is mounted on the contralateral side, and the therapy transducer is mounted on the ipsilateral side. This arrangement may have some advantages (shorter therapy beam propagation and lower therapy beam attenuation), while the registration procedure is kept exactly the same as described herein.

The imaging transducer 212 may be part of an imaging subsystem 220 that also includes the head frame 204. An alternative or additional therapy subsystem 228 likewise includes the therapy transducer 216 and the head frame 204.

As between the imaging and therapy subsystems 220, 228, FIG. 2 shows a more complete picture of the imaging subsystem, although the therapy subsystem can be analogous other than the fact that one transducer 212 is specialized for imaging and the other transducer 216 is specialized for therapy. The imaging subsystem further includes an enclosure 232 for acoustic coupling fluid and, within the enclosure, a transducer assembly 236, or may simply contain an appropriate coupling mechanism, such as that achieved using ultrasound coupling gel. The part of the enclosure 232 for contact with the patient may be a conformal coupling membrane 234. The transducer assembly 236 includes the imaging transducer 212 and its connecting motorized motion frame, or "motorized stage", 240. The imaging subsystem 220 might also include motor and transducer control cabling 244, and coupling fluid inlet-and-outlet tubings 248.

Like the imaging transducer 212, the therapy transducer 216 has a face 252 for acoustically interfacing with the temporal bone region of the head 208.

Once the imaging transducer 212 is navigated to image the ROI containing the clot or occlusion 256, navigation halts. Alternatively, the imaging transducer is scanned electronically until the occlusion is localized in its imaging plane.

A therapy beam 260 is then navigated, as seen from the navigation arrows 264, 268, to coincide with the occlusion 256.

The navigation is done under real-time image guidance. In particular, cavitation and/or bubble destruction 272 caused by the therapy beam 260 is detected via echo data from an imaging beam 276 issued by the imaging transducer 212. The navigation 264, 268 of the therapy beam 260 is halted when the detection occurs, i.e., when the cavitation and/or bubble destruction 272 is detected to be at the location of the occlusion 256 in the ROI, indicating registration between the imaging transducer 212 and the therapy transducer 216 and their respective beams (276, 260) as indicated by the radiofrequency (RF) data returned from pulses issued by the imaging transducer 212. The apparatus 100, via the MAB registration module 112, determines if and when the microbubble destruction/cavitation 272 occurs in the image frame/ROI. Depending on the result, the MAB registration module further controls the therapy transducer 216 to, via its motorized stage or electronic steering, point in a different direction automatically, until registration is achieved. Search patterns for this automated registration procedure could include a serpentine-like back and forth scanning, or spiral scanning, for example. Alternatively, the therapy transducer 216 is manually pivotable or otherwise manually movable, under interactive visual guidance of an onscreen graphic of a contour of the broad therapy beam 260. The graphic can be an overlay on B-mode imaging. Such a graphic is mentioned in the Vignon application, although the main focus in Vignon is on color-wise distinguishing between areas of stable cavitation and inertial cavitation, for patient safety. An optionally single-color graphic representative of cavitation can be based on a comparison of RF data representative of noise to RF data representative of the fundamental frequency. The fundamental image is computed by filtering RF data for the fundamental frequency and subjecting the filtered data to envelope detection. Likewise, a noise image is computed by filtering the RF data at 1.75 times the fundamental frequency and subjecting the filtered data to envelope detection. If the noise image brightness exceeds the fundamental image brightness by a certain threshold, e.g., −25 decibels (dB), cavitation and/or bubble destruction 272 is determined to exist for the voxel of, for example, the current B-mode imaging plane.

Figure 3A:
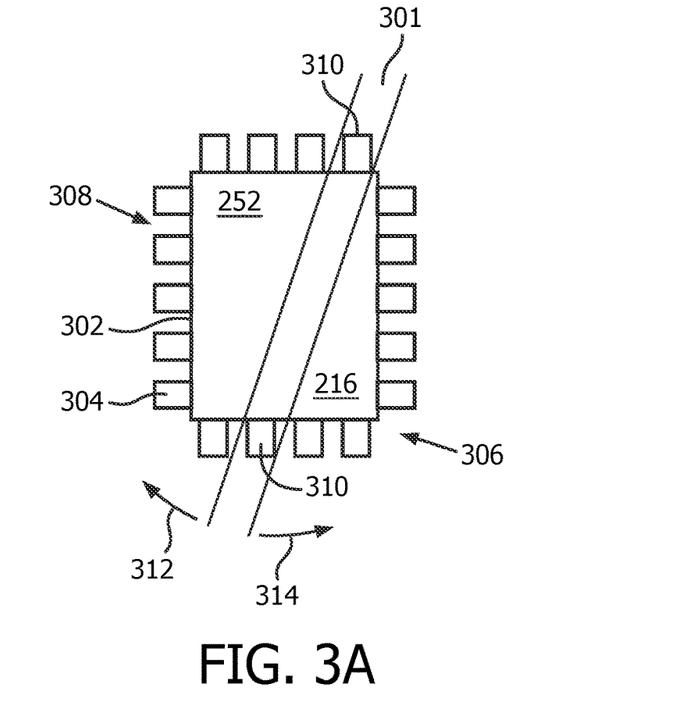
FIGS. 3A-3C are schematic and conceptual diagrams illustrative of examples of how other methods of inter-transducer registration are implementable, in accordance with the present invention.

A scenario in the inter-transducer registration embodiment is shown in FIG. 3A, and includes the therapy transducer 216, and an elevational plane 301 of an ultrasound image acquired by the imaging transducer 212. In the current example, the imaging transducer is implemented as a two-dimensional (2D) imaging transducer (with full rotational capability), although the structures in FIG. 3A are usable also in the context of imaging by matrix transducers. At a periphery 302 of the face 252 of the therapy transducer 216 are ultrasound receiving elements (or "alignment elements")

304. A series 306 of the receiving elements 304 are spaced apart from each other by gaps 308. The series 306 is configured such that at least two 310 of the elements 304, i.e., on opposite sides of the face 252, are within the elevational plane 301 irrespective of an orientation of the plane, the orientation being represented in FIG. 3A by the orientation arrows 312, 314.

Figure 3B:
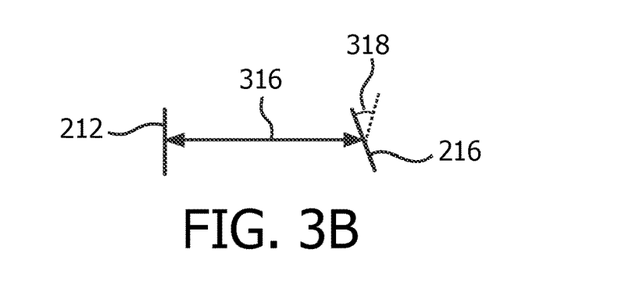

The elements 304 output content from which time of flight information on imaging pulses from the imaging transducer 212 can be derived. Referring to FIG. 3B, the time of flight data provides a distance 316 between the imaging transducer 212 and the therapy transducer 216. By distinguishing among the output of different ones, generally three or more, of the elements 304, information about an orientation 318 of the therapy transducer 216 relative to the imaging transducer 212 is available. Relative pressure magnitude of signals received by the elements 304 may also contribute to orientation determination, since an oblique-facing element receives merely a directional component as incident pressure. An algorithm for orientation determination may be empirically derived. The above calculations provide a position and relative orientation 318 of the therapy transducer 216 in the space or coordinate system of the imaging transducer 212. Accuracy of the estimated location of each of the receiving elements 304 is on the order of 1 millimeter (m), which suffices, especially for a broad therapeutic beam. Knowledge of where the clot/occlusion 256 is in the space of the imaging transducer 212 is gleaned from an initialization routine discussed below in connection to FIG. 4A. Together these two localizations in the space of the imaging transducer 212 determine a path from the therapy transducer 216 to the clot/occlusion 256. Since the position and orientation 318 of the therapy transducer 216 in the space of the imaging transducer 212 are known, the location of the clot/occlusion 256 in the space of the therapy transducer is now also known. Accordingly, with inter-transducer registration having been achieved, the therapy transducer 216 can direct a beam for treating the clot/lesion 256 and surrounding margin, as needed for the STL therapy.

Figure 3C:
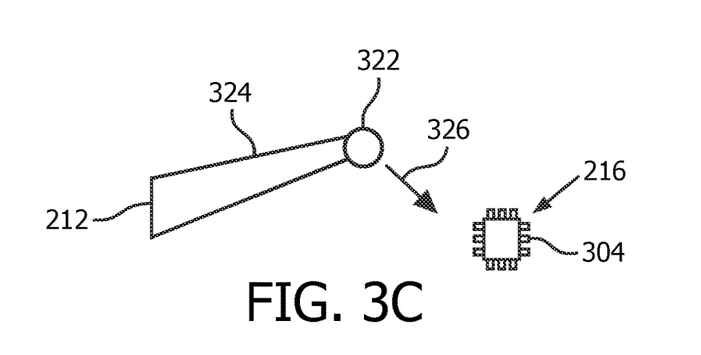

An alternative inter-transducer registration scheme 320 is conceptually depicted in FIG. 3C. A clot/occlusion 322 sufficiently offset from a temple-to-temple axis is focused upon by an imaging beam 324 from the imaging transducer 212 (or contained within the imaging plane of the imaging transducer). Side scattering 326 is detected via the elements 304 at the periphery 302 of the face 252 of the therapy transducer 216.

Figures 4A, 4B:
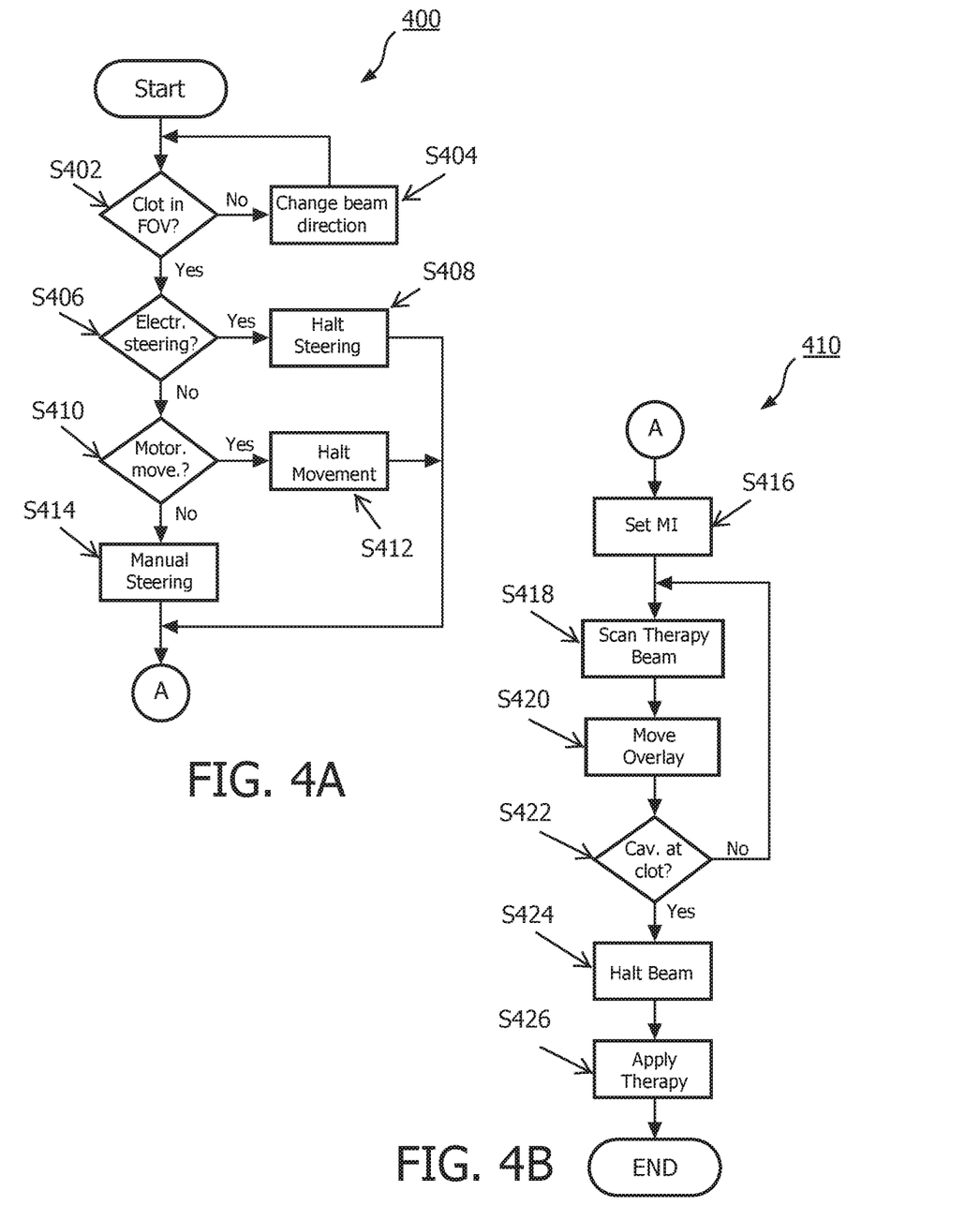
FIGS. 4A-4D are flow charts providing samples of how inter-transducer registration is operable, in accordance with the present invention.

FIG. 4A is the lesion-locating initialization routine 400 mentioned above. While the field of view of the imaging transducer 212 does not include, or centrally include, the target of the therapy, e.g., clot/occlusion 256 (step S402), the direction of the imaging beam 276 is changed (step S404). When the clot/occlusion 256 is imaged, or imaged sufficiently well (step S402), if the beam direction has been changed by electronic steering (step S406), the steering is halted (step S408). If, on the other hand, steering of the beam 276 has been by motorized movement (step S410), the motorized movement is halted (step S412). Otherwise, if steering has been manual (step S414), i.e., by clinician manual manipulation of the imaging transducer 212 under interactive onscreen visual guidance (in an embodiment that does not use a fluid-filled enclosure), the clinician manually fixes the imaging transducer in place by, for example, tightening a locking knob on the head frame 204 (step S414). An alternative routine involves preparing computed tomography (CT) and/or magnetic resonance imaging (MR) images, identifying the clot/occlusion in the images, and registering the images with the space of the ultrasound imaging transducer 212.

FIG. 4B is a microbubble-activity-based registration process 410. It is performed just after the lesion-locating initialization routine 400, which has just localized the clot/occlusion in the imaging transducer's image. The mechanical index (MI) is set to approximately 0.3 (or larger, sufficient to cavitate the microbubbles in circulation) (step S416). Mechanical index is defined here as peak negative pressure (in [MPa]) divided by the square root of the ultrasound frequency (in [MHz]), and is indicative of the probability of bubble destruction. The therapy beam 260 is scanned manually, electronically or by motor (step S418). Optionally, a beam contour overlay is moved in synchrony on the display (step S420). In particular, cavitation imaging provides a dynamic signal representative of the cavitation and/or microbubble destruction 272 and by which the cavitation and/or bubble destruction is spatially trackable in real time. If cavitation and/or bubble destruction 272 is occurring at the location of the clot/occlusion (or just next to it) as seen in the ongoing imaging (step S422), navigation of the therapy beam 260 is halted (and locked in place if it has been scanned manually) (step S424) and therapy is now applied to the clot/occlusion 256 (step S426). Otherwise, if cavitation and/or bubble destruction 272 monitoring is to continue (step S422), processing branches back to the therapy beam scanning step S418.

Figure 4C:
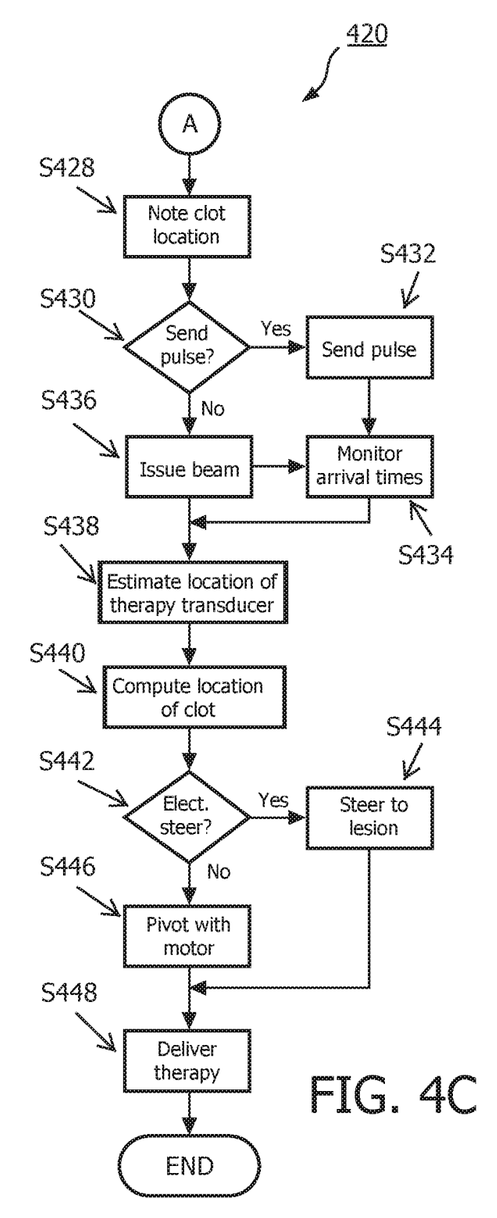

FIG. 4C is representative of a transducer-space-based type of receiving-element-based (REB) registration 420. It is preceded by the lesion-locating initialization routine 400, which has just localized the clot/occlusion in the imaging plane. The location of the clot/occlusion in the space of the imaging transducer 212 is noted (step S428). If a single, spherically propagating, unfocused pulse is to be sent for detection via the receiving elements 304 (step S430), the pulse is sent (step S432) and the different arrival times of this single pulse to respective elements 304 are monitored (step S434). Otherwise (step S430), spatially directed, focused beams in, via electronic steering, many directions to target individual elements 304 are issued by the imaging transducer 212 (step S436). For example, an elevational plane of an ultrasound image may be electronically rotated as indicated by the orientation arrows 312, 314. The elements receive, during the rotating, a radiofrequency signal for detection of when, during the rotating, the received signal is maximal. The rotation, reception and detection may all be performed automatically and without need for user intervention. Or the clinician may manually rotate the plane. In the plane of maximal reception, the content of the received ultrasound is analyzed. Responsive to any one of the above alignment sequences (steps S430-S436), the REB registration module 108 analyzes the content of the received ultrasound to make an estimate of the location and orientation 318 of the therapy transducer 216 in the space of the imaging transducer 212 (step S438). Based on the estimates, the REB registration module 108 computes the location of the clot/occlusion in the space of the therapy transducer 216, as mentioned herein above (step S440), thus achieving transducer registration. If the therapy beam 260 is to be electronically steered (step S442), it is steered to the lesion 256 (step S444). If, on the other hand, the therapy beam 260 is not to be electronically steered (step S442), it is pivoted into the direction of the clot/occlusion 256 by means of a motor (step S446). In either event, the therapy transducer is locked in place if it has been scanned manually, and the therapy beam 260 is applied to deliver therapy to the clot/occlusion 256 (step S448).

Figure 4D:
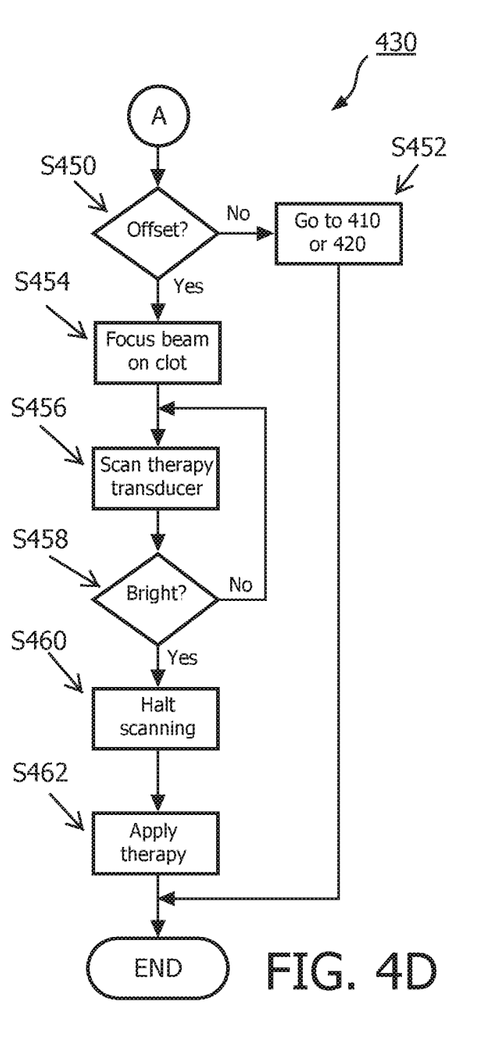

An ultrasound-scattering-based type of receiving-element-based (REB) registration 430 is shown in FIG. 4D. If the clot/occlusion location determined in the lesion-locating initialization routine 400 is sufficiently offset from the temple-to-temple axis (step S450), the process 430 is usable; otherwise another method, such as those described immediately herein above is to be used (step S452). If the offset is sufficient (step S450), the REB registration module 108 causes the imaging transducer 212 to focus the imaging beam 276 on the clot/occlusion 256 (step S454). The therapy transducer 216 is scanned with the receiving elements 304 active to detect side-scattering from the clot/occlusion 256 (step S456). The scanning can be electronic, motorized or manual. If the currently detected side scattering has a brightness that is detected, or maximal (step S458), the scanning halts (with the therapy transducer 216 being locked in place if it has been scanned manually) (step S460) and therapy is applied (step S462). Otherwise, if the side scattering is not currently detected, or is not maximal (step S458), processing returns to the scanning step S456.

For both receiving-element-based processes 420, 430, the therapeutic sequence may be interrupted at regular intervals (automatically) during treatment, and the imaging transducer 212 controlled (automatically) to send out the unfocused pulse or alignment pulse sequences that are received by the receiving elements 304, to verify that both devices 212, 216 are still aligned. If alignment remains intact, the treatment is resumed. If both devices have drifted out of alignment (due to patient and/or head frame motion, for example), the treatment can be interrupted, and the alignment procedure can be repeated by the clinician. In the case of the motorized transducer assembly 236, or a matrix ultrasound array implementation, such process could occur without operator intervention.

What is proposed herein above can find application in image guidance of any ultrasound beams pointed at each other (as in the current application when mounted on the skull for STL therapy), for ultrasound therapy and diagnosis (e.g., Transcranial Doppler (TCD)). One particular area is for ischemic stroke therapy using any of the existing ultrasound systems, or a dedicated device designed for emergency vehicle use. Additional uses for the proposed technology could include a novel treatment for blast-induced traumatic brain injury (bTBI) or mild traumatic brain injury (mTBI); neuro-protective treatments using ultrasound and microbubbles; and in drug delivery to the brain using ultrasound, systemically injected drug agents and microbubbles, enhancing the transport of the drugs across the blood-brain barrier using appropriately targeted and defined ultrasound exposures.

An apparatus for ultrasound irradiation of a body part includes a first ultrasound transducer, and a second ultrasound transducer mounted oppositely with respect to the body part, and is configured: a) such that at least two ultrasound receiving elements, for determining a relative orientation of the first to the second transducer, are attached to the first transducer; b) for a beam, from the first transducer, causing cavitation, and/or bubble destruction of systemically circulating microbubbles, within the body part; or c) both with the attached elements and for the causing. The apparatus registers, with said first transducer, the second transducer, by using as a reference respectively the features a) and/or b). A detachable subsystem includes either a therapy or imaging transducer, to form a combination imaging and therapy system, the subsystem being configured for removable coupling to correspondingly an imaging or therapy subsystem comprising a head frame to which is mounted an imaging or therapy transducer, the imaging or therapy subsystem for registering the imaging or therapy transducer, one to the other, by the above method.

While the invention has been illustrated and described in detail in the drawings and foregoing description, such illustration and description are to be considered illustrative or exemplary and not restrictive; the invention is not limited to the disclosed embodiments.

For example, the detachable ultrasound subsystem 136, 152 can further include an amplifier, pulsing electronics and control electronics, and can be designed as a standalone/separate unit, with only loose coupling to correspondingly the imaging or therapy subsystem 132, 148 via a serial interface, network link, or similar connection. Also, although the above examples relate to intra-cranial examination and treatment, what is proposed herein is not limited to intra-cranial applications. The innovative technology can extend to real-time inter-transducer registration in examination/treatment of other body parts. Nor is the intended scope of what is proposed herein above limited to treatment of clots or occlusions. Ultrasound mediated drug delivery, for example and as noted herein above, is a possible application.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. Any reference signs in the claims should not be construed as limiting the scope.

A computer program can be stored momentarily, temporarily or for a longer period of time on a suitable computer-readable medium, such as an optical storage medium or a solid-state medium. Such a medium is non-transitory only in the sense of not being a transitory, propagating signal, but includes other forms of computer-readable media such as register memory, processor cache, RAM and other volatile memory.

A single processor or other unit may fulfill the functions of several items recited in the claims. The mere fact that certain measures are recited in mutually different dependent claims does not indicate that a combination of these measures cannot be used to advantage.

What is claimed is:

1. An apparatus for ultrasound irradiation of a body part, said apparatus comprising:
   a first ultrasound transducer configured to be mounted on a first side of the body part, the first ultrasound transducer comprising:
   a face comprising a plurality of ultrasound transducer elements configured to apply a therapy beam to the body part; and
   a series of ultrasound receiving elements surrounding a periphery of the face;
   a second ultrasound transducer configured to be mounted on a second side of the body part opposite the first side and spaced apart from the first transducer, wherein the second ultrasound transducer is configured to generate an elevational plane of an ultrasound image by emitting one or more imaging pulses,
   and automatically and without need for user intervention electronically rotate the elevational plane of the ultrasound image, and wherein the first ultrasound transducer is further configured to, during said rotating, receive a radio frequency (RF) signal via said series of ultrasound receiving elements; and
a receiving-element-based (REB) module including a processor, wherein the REB is configured to receive the RF signal from the first ultrasound transducer and determine a location and an orientation of the first ultrasound transducer relative to the second transducer, wherein the location is based, at least in part, on time of flight of the imaging pulses derived from the RF signal from at least two of the series of ultrasound receiving elements, wherein the at least two of the series of ultrasound receiving elements are located on opposite sides of the face of the first transducer, and
wherein the orientation is based, at least in part, on the RF signal from three or more of the series of ultrasound receiving elements.

2. The apparatus of claim 1, further comprising a motorized assembly configured to move the first ultrasound transducer to point in a different direction until an alignment criterion is met, based on an output of said series of ultrasound receiving elements.

3. The apparatus of claim 1, further configured for three-dimensional imaging via said second ultrasound transducer.

4. The apparatus of claim 1, wherein said location and said orientation is determined, at least in part, by focusing, via said second ultrasound transducer, on a specific target within said body part and using two or more of said series of ultrasound receiving elements for detecting side scattering from said target.

5. The apparatus of claim 1, wherein the therapy beam is configured to cause cavitation and/or bubble destruction, wherein the REB module is further configured to determine the location and the orientation, based, at least in part on a location of said cavitation and/or said destruction.

6. The apparatus of claim 5, wherein said first ultrasound transducer is further configured to scan the therapy beam; and
wherein said second ultrasound transducer is further configured to monitor an outcome of said cavitation and/or bubble destruction.

7. The apparatus of claim 6, wherein said first ultrasound transducer is configured to perform the scan automatically and without need for user intervention, until, based on imaging via said second ultrasound transducer, it is determined by a microbubble-activity-based (MAB) registration module including a second processor, based on imaging of said cavitation and/or bubble destruction, that a current direction of said scan brings the therapy beam to a location of the elevational plane of the ultrasound image.

8. The apparatus of claim 1, wherein the second ultrasound transducer is held fixed in place during said rotating.

9. The apparatus of claim 1, further comprising a head frame configured for the mounting of both the first ultrasound transducer and the second ultrasound transducer, wherein said apparatus is configured to determine said location and said orientation while said head frame is worn on said body part.

10. The apparatus of claim 9, wherein said second ultrasound transducer is movably mounted to said head frame, and the location and said orientation are determined, at least in part, by fixing said second ultrasound transducer in place in said head frame.

11. The apparatus of claim 9, wherein said first ultrasound transducer is movably mounted to the head frame, wherein said apparatus is further configured for mechanical movement of said first ultrasound transducer to scan a volume within said body part.

12. The apparatus of claim 1, further comprising a display, said apparatus further configured for imaging said body part via said second ultrasound transducer and for displaying, via said display, an image of said body part.

13. The apparatus of claim 1, wherein the location and orientation are based, at least in part, on when said RF signal is maximal during said rotating of the second ultrasound transducer.

14. A non-transitory computer readable medium embodying a computer program for ultrasound irradiation of a body part via an apparatus, said apparatus comprising:
a first ultrasound transducer configured to be mounted on a first side of the body part, the first ultrasound transducer comprising:
a face comprising a plurality of ultrasound transducer elements configured to apply a therapy beam to the body part; and
a series of ultrasound receiving elements surrounding a periphery of the face of the first ultrasound transducer;
a second ultrasound transducer configured to be mounted on a second side of the body part opposite the first side and spaced apart from the first transducer, wherein the second ultrasound transducer is configured to generate an elevational plane of an ultrasound image by emitting one or more imaging pulses;
said program having instructions executable by a processor for performing a plurality of acts, among said acts there being the acts of:
automatically and without need for user intervention electronically rotate the elevational plane of the ultrasound image of the second transducer;
during said rotating, receive a radio frequency (RF) signal via said series of ultrasound receiving elements of the first transducer; and
determine a location and an orientation of the first ultrasound transducer relative to the second transducer, wherein the location is based, at least in part, on time of flight of the imaging pulses derived from the RF signal from at least two of the series of ultrasound receiving elements, wherein the at least two of the series of ultrasound receiving elements are located on opposite sides of the face of the first transducer, and
wherein the orientation is based, at least in part, on the RF signal from three or more of the series of ultrasound receiving elements.

15. A detachable ultrasound subsystem comprising:
a head frame;
an imaging transducer and a therapy transducer removably mounted to opposite sides of said head frame; and
a processor, wherein said processor is configured for:
determining a location and an orientation of the therapy transducer relative to the imaging transducer, wherein said determining comprises:
rotating an elevational plane of an ultrasound image of the imaging transducer; and
receiving a radio frequency (RF) signal via a series of ultrasound receiver elements surrounding a periphery of a face of the therapy transducer, wherein the RF signal is responsive to the elevational plane of the ultrasound image,
wherein the location is based, at least in part, on time of flight of ultrasound signals associated with the elevational plane of the ultrasound image derived from the RF signal from at least two of the series of ultrasound receiving elements, wherein the at least two of the series of ultrasound receiving elements are located on opposite sides of the face of the first transducer, and wherein the orientation is based, at least in part, on the RF signal from three or more of the series of ultrasound receiving elements.

\* \* \* \* \*